United States Patent [19]

Lamb et al.

[11] Patent Number: Plant 5,723

[45] Date of Patent: Apr. 22, 1986

[54] APPLE CULTIVAR NY 58533-1

[75] Inventors: Robert C. Lamb; Herb S. Aldwinckle, both of Geneva, N.Y.

[73] Assignee: Cornell Research Foundation, Inc., Ithaca, N.Y.

[21] Appl. No.: 562,059

[22] Filed: Dec. 16, 1983

[51] Int. Cl.[4] ..... A01H 5/03

[52] U.S. Cl. ..... Plt./34

[58] Field of Search ..... Plt./34

*Primary Examiner*—Robert E. Bagwill

[57] ABSTRACT

A new and distinct apple cultivar, named 'Freedom' which is exceptional for its resistance to apple scab incited by *Venturia inaequalis,* cedar apple rust incited by *Gymnosporangium juniperi virginianae,* apple powdery mildew incited by *Podosphaera leucotricha,* and fire blight incited by *Erwinia amylovora,* for its high yields of large fruits and for its good quality.

4 Drawing Figures

SUMMARY

This invention is a new and distinct cultivar of the apple which is exceptional for its resistance to apple scab incited by *Venturia inaequalis,* cedar apple rust incited by *Gymnosporangium juniperi virginianae,* apple powdery mildew incited by *Podosphaera leucotricha,* and fire blight incited by *Erwinia amylovora,* for its high yields of large fruits and for its good quality.

ORIGIN

This new cultivar was developed under project 451 Breeding Disease Resistant Apple Cultivars, of the Dept. of Pomology and Viticulture and the Dept. of Plant Pathology of the New York State Agricultural Experiment Station, Geneva, N.Y. It was selected from a cross made in 1958 of NY 18491 (Macoun×Antonovka) pollinated by NY 49821–46 (Golden Delicious×Ill 26829-2-2). It was selected for further trial, and first propagated in 1965. It has been extensively tested since that time under the number NY 58553-1. It will be named Freedom.

BRIEF DESCRIPTION OF PHOTOGRAPHS

DESCRIPTION

'NY 58553-1' has been extensively tested in the greenhouse and in the orchard for resistance to the major apple diseases. It is highly resistant to apple scab, when inoculated in the greenhouse, showing only small, nonsporulating, necrotic spots on the inoculated leaves. In the orchard no symptoms of apple scab have ever been found on this cultivar. In greenhouse tests of cedar apple rust resistance, NY 58553-1 showed pycnia of this disease after inoculation but we have only seen rust symptoms once on this cultivar in the field. For fire blight following inoculation in the greenhouse NY 58553-1 was given a score of 2 which is a resistant rating. In the orchard on the USDA scale from 1 to 10 "8" is the worst fire blight infection that has been observed. This means that there is some entry into 2 year old wood and that not more than 4–6% of the tree was infected.

We do not have a good greenhouse technique for evaluating resistance to mildew in apples. However, NY 58553-1 has been evaluated for resistance in unsprayed orchards for many years. Lesions of mildew can be found on the leaves in most years but the occurrence of infected terminals on which the disease usually overwinters is quite rare.

The level of resistance to these 4 major diseases is such that this variety can be grown without any protective sprays in this area. It is not resistant to insects and must be sprayed with insecticides to protect it from insect pests.

Figure 1:
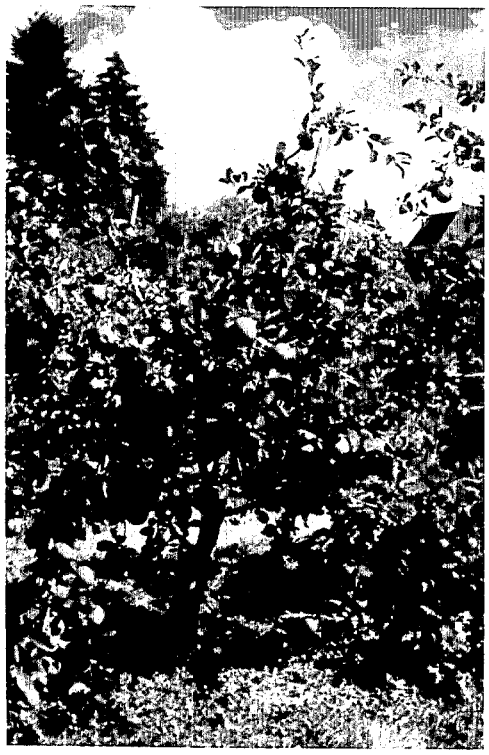
FIG. 1 is 'Freedom'/EM9 in its 8th leaf, approximately 7 feet tall.

The habit of growth of NY 58553-1 is vigorous and spreading. See FIG. 1. It is precocious and very productive. The shoots are a deep red in color, nearly glabrous at the base and tomentose toward the tip. The lenticels are prominent, scattered, grey in color and oval in shape with the long axis parallel to the shoot. Most of the buds on one year old shoots will break in the spring to form spurs. These spurs will remain productive for 2–3 years.

The leaves of this variety are large, 102×63 mm and leathery in texture. The shape of the leaf is elliptic, the apex is acuminate, the base is obtuse, and the margins are coarsely serrate. The upper leaf surface is glabrous and dark green in color and the lower surface is tomentose and greyish green. The shoots are reddish in color nearly glabrous at the base and tomentose toward the tip.

'NY 58553-1' blooms on the average May 15 or about 3 days after McIntosh. It has fertile pollen and is a precocious and productive variety.

Figure 2:
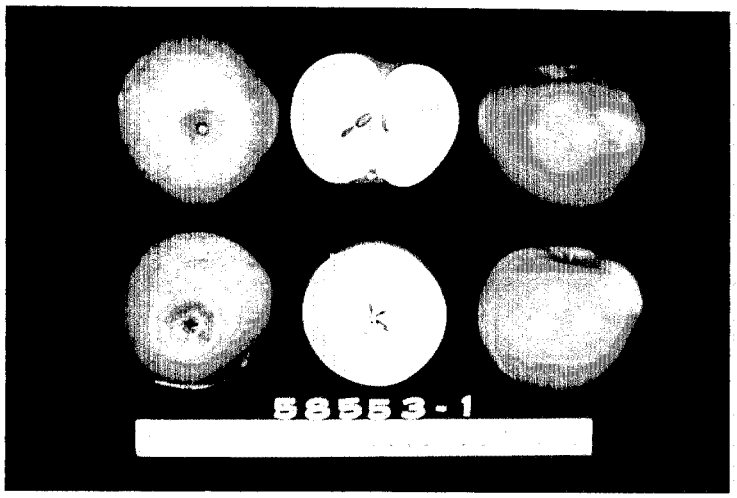
FIG. 2 is the fruit of 'Freedom' showing stem end, calyx end, side view, cross and longitudinal sections.
Figure 3:
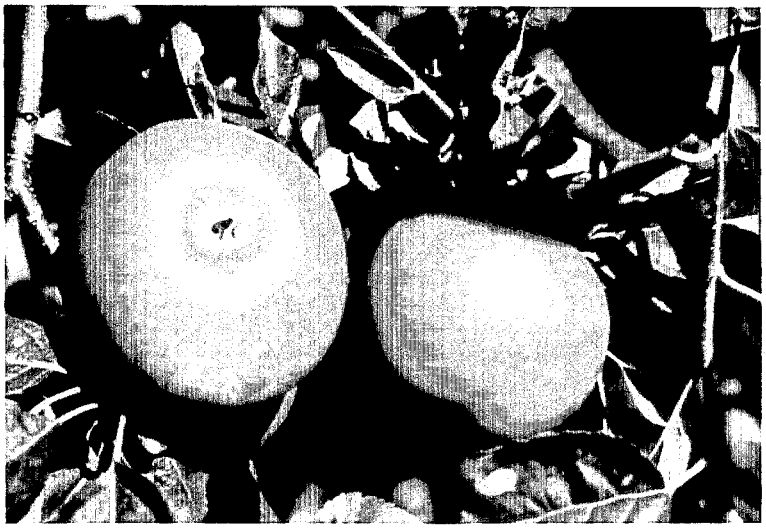
FIG. 3 is the fruit of 'Freedom' on the tree.
Figure 4:
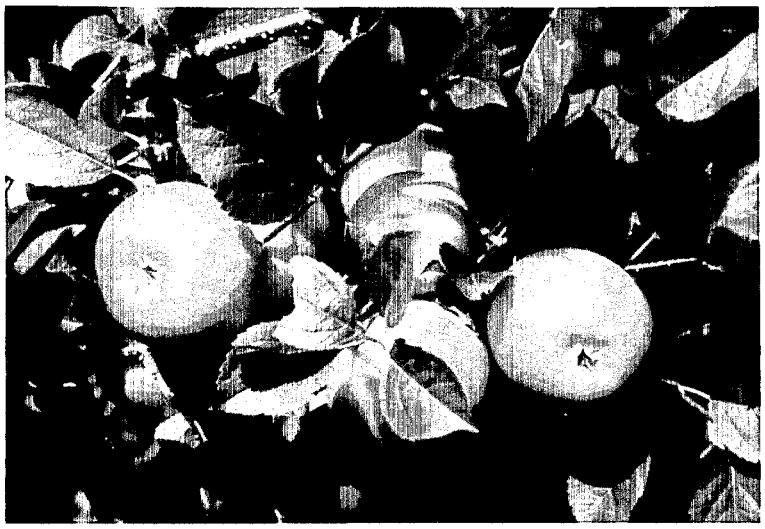
FIG. 4 is the fruit of 'Freedom' on the tree.

The fruit of NY 58553-1 (FIGS. 2, 3, 4) is large, 69 mm long, and 85 mm in the largest cross-sectional diameter, and oblate in shape. It ripens October 5. Approximately 80% of the surface is covered with bright red. This red is characterized by readings of Lightness 41.41, Chroma 32.00 and Hue 21.27 on the Hunter Color Difference Meter using the pink standard plate C2 9647. (Hunter Associates Lab Inc., Fairfax, VA). The ground color is yellow. The cavity is deep, medium broad, acute, and russetted. The stem is approximately 20 mm long and slender. The calyx is large and open in a medium deep wide cavity. The calyx tube is short, wide, and conical. The flesh is cream colored, firm, medium-fine, tender and juicy in texture. The flavor is sprightly sub-acid and the quality is good.

Isozyme genotype: The apple cultivar 'Freedom' was one of 54 distinct cultivars characterized for isozyme genotype in 6 isozyme systems. The results of the complete study have been submitted for publication in the Journal of the American Society for Horticultural Science. An abbreviated description of the methods used and the genotype determined for 'Freedom' will be presented below.

Materials and methods: Young leaf tissue was thoroughly crushed in ice cold 0.05M tris-maleate pH 8.5 containing 20% glycerol (v/v) 10% soluble polyvinylpyrolidone, 0.5% Triton X-100 and 14 mM 2-mercaptoethanol. The extracts were subjected to horizontal starch gel electrophoresis on a tris citrate/lithium borate system at pH 8.1 (Selander et al., 1971) and on a histidine gel at pH 6.5 (Cardy et al., 1980). Slices from the tris citrate/lithium borate gel were assayed for aspartate aminotransferase, glucose phosphate isomerase and triose phosphate isomerase. Diaphorase, 6-phosphogluconate dehydrogenase and isocitrate dehydrogenase were assayed on slices from the histidine gel. The assay conditions were minor modification of standard recipes given in Shaw and Prasad (1970) and Vallejos (1983). Most of the assays were also described in Chyi and Weeden (1984).

The cultivar 'Freedom' exhibited specific and invariant genotypes at each of the loci identified in Table I. The genotype of 'Freedom' as well as another common cultivar with at least one allele in common with Freedom are also given in the Table. The isozyme phenotype was uniform among all 'Freedom' trees sampled and could be determined as long as healthy young leaves were available.

TABLE I

| | Freedom isozyme genotypes. | |
|---|---|---|
| Isozyme[1] | Genotype[2] | Cultivars possessing similar alleles[3] |
| 6PGD-1 | ad | Delicious (ac); Golden Delicious (dd) |
| 6PGD-2 | normal | Delicious and Golden Delicious |
| AAT-1 | bc | Delicious (bc) |
| AAT-2 | cc | Delicious (cc) |
| GPI-2 | bc | Delicious (cc) (b allele unique to 'Freedom') |
| TPI-2 | ab | Golden Delicious (bc) |
| DIAP | ab | Delicious (ab) |
| IDH-1 | bb | Golden Delicious (bb) |
| IDH-2 | aa | Golden Delicious (aa) |

[1]As defined in Weeden, N. F. and R. C. Lamb (submitted).
[2]As defined in Weeden, N. F. and R. C. Lamb (submitted).
[3]Genotype of cultivar given in parentheses.

References cited above

Cardy, B. J., C. W. Stuber, and M. M. Goodman, 1980. Techniques for starch gel electrophoresis of enzymes from maize (*Zea mays* L.). Dept. of Stat. Mimeo Series No. 1317, North Carolina State Univ., Raleigh.

Chyi, Y. S. and N. F. Weeden, 1984. Relative isozyme band intensities permit the identification of the 2N gamete parent for triploid apple cultivars. HortScience 19:(in press).

Selander, R. K., M. H. Smith, S. Y. Yang, W. E. Johnson, and J. B. Gentry, 1971. Biochemical polymorphism and systematics in the genus Peromyscus. I. Variation in the old-field mouse (*Peromyscus polionotus*). Studies in Genetics VI. Univ. Texas Publ. 7103:49–90.

Shaw, C. R. and R. Prasad, 1970. Starch gel Electrophoresis — A compilation of recipes. Biochem. Genet. 4:297–320.

Vallejos, C. E., 1983. Enzyme activity staining. In:Isozymes in plant genetics and breeding. Part A. S. D. Tanksley and T. J. Orton (eds.). Elsevier, Amsterdam, pp. 469–516.

Merits: The most outstanding features of NY 58553-1 are its resistances to the four major disease of apple in this area. It is highly resistant to apple scab and moderately resistant to fire blight, cedar apple rust, and powdery mildew. It is not necessary to spray with fungicides or bactericides in most years.

This apple is also meritorious for its precocious and high yielding characteristics, its large fruit size, and good quality.

We claim:

1. The new and distinct apple variety herein described and illustrated and identified by the characters enumerated above.

* * * * *